(12) United States Patent
Berthon-Jones

(10) Patent No.: US 8,967,149 B2
(45) Date of Patent: *Mar. 3, 2015

(54) METHOD AND APPARATUS FOR ADJUSTING RESPIRATORY MASK SEALING FORCE

(71) Applicant: ResMed Limited, Bella Vista (AU)

(72) Inventor: Michael Berthon-Jones, Leonay (AU)

(73) Assignee: ResMed Limited, Bella Vista (AU)

( * ) Notice: Subject to any disclaimer, the term of this patent is extended or adjusted under 35 U.S.C. 154(b) by 235 days.

This patent is subject to a terminal disclaimer.

(21) Appl. No.: 13/733,185

(22) Filed: Jan. 3, 2013

(65) Prior Publication Data

US 2013/0133657 A1 May 30, 2013

Related U.S. Application Data

(63) Continuation of application No. 11/666,869, filed as application No. PCT/AU2005/001711 on Nov. 9, 2005, now Pat. No. 8,360,062.

(60) Provisional application No. 60/626,487, filed on Nov. 10, 2004.

(30) Foreign Application Priority Data

Nov. 9, 2005 (AU) ................. PCT/AU2005/001711

(51) Int. Cl.
*A62B 18/08* (2006.01)
*A61M 16/06* (2006.01)
(Continued)

(52) U.S. Cl.
CPC ........... *A61M 16/0683* (2013.01); *A61M 16/06* (2013.01); *A61M 16/0066* (2013.01);
(Continued)

(58) Field of Classification Search
CPC ............ A61M 16/06; A61M 16/0605; A61M 2016/0661; A61M 16/0616; A61M 16/0611; A61M 16/20; A61M 2205/3331
USPC ............. 128/206.21, 206.23, 206.24, 206.26, 128/206.28, 201.29, 202.19; 601/148, 151, 601/152; 602/13
See application file for complete search history.

(56) References Cited

U.S. PATENT DOCUMENTS 2,390,233 A 12/1945 Akerman et al.
2,666,432 A 1/1954 Stanton
(Continued)

FOREIGN PATENT DOCUMENTS

AU 200071882 6/2001
DE 37 07 952 9/1988
(Continued)

OTHER PUBLICATIONS

Notice of Reasons for Rejection Mailed Jan. 25, 2011 in Japanese Application No. 2007-540453, including English translation (8 pages).
(Continued)

*Primary Examiner* — Kristen Matter
(74) *Attorney, Agent, or Firm* — Nixon & Vanderhye P.C.

(57) ABSTRACT

A mask assembly includes a mask with an inflatable bladder. The internal pressure of the inflatable bladder can be set to be higher than the delivered therapeutic pressure. The pressure offset may be constant, or it may vary over the range of therapeutic pressures. Thus, the force necessary to maintain a contact seal between the mask and the patient can be reduced, thereby providing a system that is more comfortable to the patient, which increases patient compliance.

26 Claims, 14 Drawing Sheets

(51) Int. Cl.
*A61M 16/00* (2006.01)
*A61M 16/08* (2006.01)
*A61M 16/20* (2006.01)

(52) U.S. Cl.
CPC ....... *A61M16/0816* (2013.01); *A61M 16/0875* (2013.01); *A61M 16/20* (2013.01); *A61M 16/065* (2014.02); *A61M 16/0694* (2014.02); *A61M 2205/3331* (2013.01)
USPC .................... 128/206.24; 128/206.26

(56) References Cited

U.S. PATENT DOCUMENTS

| | | | |
|---|---|---|---|
| 2,824,557 | A | 2/1958 | Mejean et al. |
| 2,875,757 | A | 3/1959 | Galleher, Jr. |
| 4,403,608 | A | 9/1983 | Warncke |
| 4,799,477 | A | 1/1989 | Lewis |
| 4,928,835 | A | 5/1990 | Collette et al. |
| 4,971,051 | A | 11/1990 | Toffolon |
| 5,074,297 | A | 12/1991 | Venegas |
| 5,421,326 | A | 6/1995 | Rankin et al. |
| 5,492,108 | A | 2/1996 | Smith et al. |
| 5,960,494 | A | 10/1999 | Gilliland et al. |
| 6,029,660 | A | 2/2000 | Calluaud et al. |
| 6,651,661 | B2 | 11/2003 | Matioc |
| 6,772,760 | B2 | 8/2004 | Frater et al. |
| 6,834,650 | B1 | 12/2004 | Fini et al. |
| 6,837,239 | B2 | 1/2005 | Beizndtsson et al. |
| 7,007,696 | B2 | 3/2006 | Palkon et al. |
| 7,243,652 | B2 | 7/2007 | Chang |
| 7,273,052 | B2 | 9/2007 | Gossweiler |
| 8,360,062 | B2 * | 1/2013 | Berthon-Jones ......... 128/206.24 |
| 2002/0029780 | A1 | 3/2002 | Frater et al. |
| 2002/0096175 | A1 | 7/2002 | Her |
| 2003/0172932 | A1 | 9/2003 | Matioc |
| 2004/0083534 | A1 | 5/2004 | Ruiz et al. |
| 2004/0118406 | A1 | 6/2004 | Lithgow et al. |
| 2004/0194783 | A1 | 10/2004 | McAuliffe et al. |
| 2004/0211428 | A1 | 10/2004 | Jones |
| 2006/0118117 | A1 | 6/2006 | Berthon-Jones |
| 2006/0185675 | A1 | 8/2006 | Colin |
| 2008/0099023 | A1 | 5/2008 | Berthon-Jones |

FOREIGN PATENT DOCUMENTS

| | | |
|---|---|---|
| EP | 0 181 842 | 5/1986 |
| NZ | 232296 | 1/1990 |
| WO | WO 00/53265 A1 | 9/2000 |
| WO | 2004/041342 | 5/2004 |
| WO | 2004/096332 | 11/2004 |
| WO | 2005/028010 | 3/2005 |

OTHER PUBLICATIONS

Examination Report Mailed Dec. 20, 2010 in New Zealand Application No. 589737 (2 pages).

Examiner's Report No. 2 mailed Aug. 11, 2011 in Australian Application No. 2005304270 (3 pages).

Decision of Rejection mailed Nov. 1, 2011 in Japanese Application No. 2007-540453, with English Translation (4 pages).

Extended European Search Report mailed Apr. 2, 2012 in European Appln. No. 05801087.7 (7 pages).

Australian Search Report issued for Australian Patent Application No. 2005304270, dated Jul. 12, 2010.

International Search Report for PCT/AU2005/001711 mailed Dec. 19, 2005.

* cited by examiner

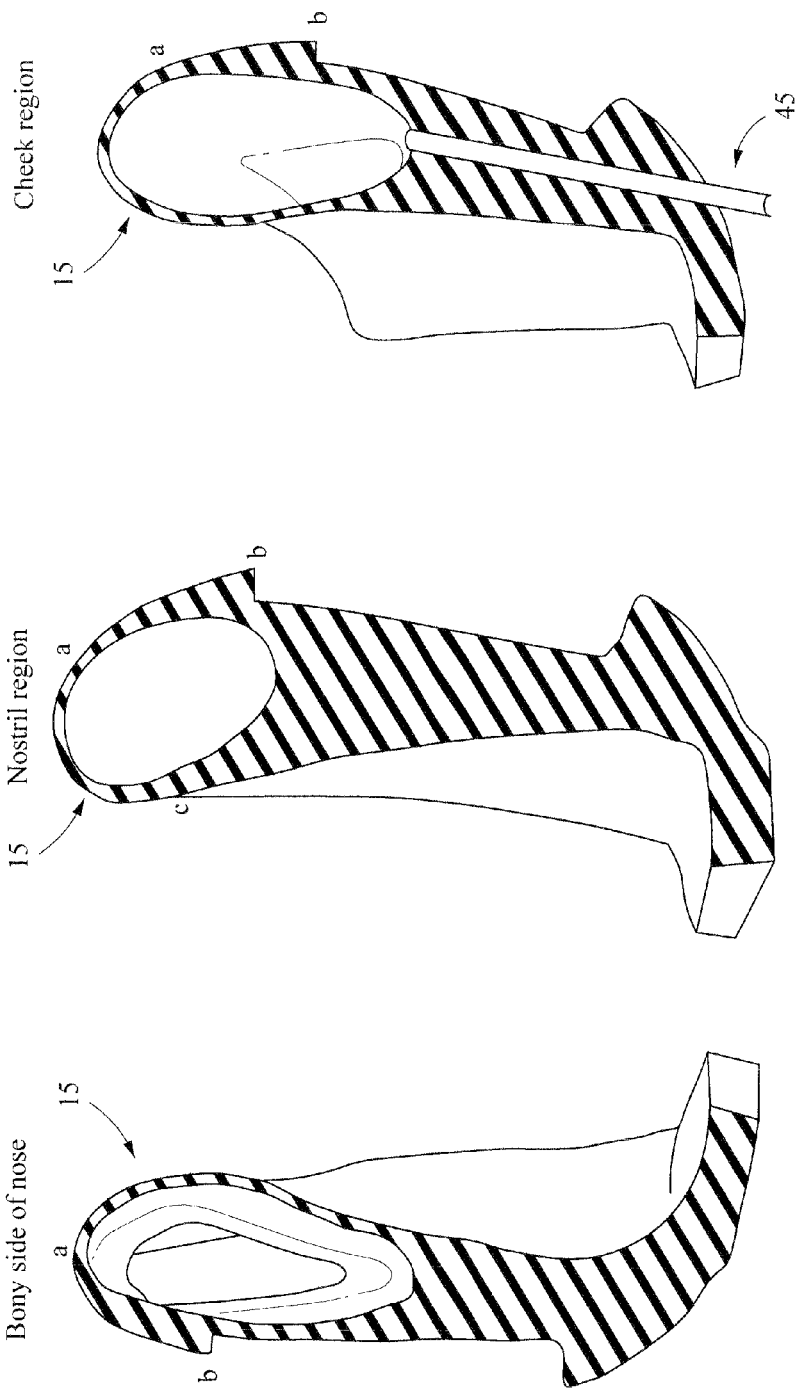

METHOD AND APPARATUS FOR ADJUSTING RESPIRATORY MASK SEALING FORCE

CROSS-REFERENCES TO RELATED APPLICATIONS

This application is a continuation of U.S. Ser. No. 11/666,869, filed May 3, 2007, now U.S. Pat. No. 8,360,062, which is the U.S. national phase of international application PCT/AU2005/001711, filed 9 Nov. 2005, which designated the U.S. and claims the benefit of U.S. Provisional Application No. 60/626,487, filed Nov. 10, 2004, each of which is incorporated herein by reference in its entirety.

BACKGROUND OF THE INVENTION

Noninvasive positive pressure therapy is used for a variety of conditions including obstructive sleep apnea, central sleep apnea, and respiratory insufficiency. In respiratory insufficiency, the most common form of relevant therapy is bilevel therapy, in which a higher pressure (typically 15-25 $cmH_2O$) is supplied during inspiration, and a lower pressure (typically around 5 $cmH_2O$) is supplied during expiration. For central sleep apnea, an advanced therapy is adaptive servo-ventilation, where a complex pressure waveform is delivered, whose amplitude is constantly adjusted, spending much time around 5-10 $cmH_2O$, but occasionally increasing to 20 $cmH_2O$. For obstructive sleep apnea, advanced devices also vary the mask pressure during the night.

In all cases, the mask must be tightened sufficiently to seal against the highest pressure used. Consider, for example, a typical facemask, in which the area under the seal is 80 $cm^2$.

If, for example, the highest pressure used is 25 $cmH_2O$, then for a typical facemask, with a contact area of about 80 $cm^2$, the total tension in the straps must exceed 25×80=2000 grams force (gF). (For a practical mask, which may not precisely fit the face, the force will need to be yet higher, in order to deform the mask and skin to seal. This additional conforming force will be discussed later.) Continuing the example, if the lowest pressure encountered is 5 $cmH_2O$, then a total strap tension of only 5×80=400 gF is required to seal at this lowest pressure. Thus, in this example, if the mask seals at the highest pressure, then an excess force of 2000−400=1600 gF is applied at the lowest pressure. With a typical respiratory cycle, where 60% of the breath is at the lowest pressure, this excess force of 1600 gF is applied to the skin over the bony structures of the face for 60% of the respiratory cycle. In the case of adaptive servo-ventilation, where the highest pressure is required for only a very small part of the night, the excess force is applied for the greater part of the night.

This excess force causes considerable discomfort, and in not uncommon cases, actually causes breakdown of the skin, for example over the bridge of the nose.

Various methods for reducing this excess force have been proposed. All do mechanical work on the elastic elements of the mask and headgear, thus pulling the mask tighter as the mask therapeutic pressure increases, and releasing the mask as the mask pressure decreases. Such methods include a bladder in the top strap or a bladder (pneumatic pillow) between the rear strap and the back of the head (see, e.g., PCT Application No. PCT/AU03/01471 to inventors Michael Berthon-Jones et al. filed Nov. 6, 2003, incorporated herein by reference in its entirety), or a bellows in the body of the mask itself (see, e.g., U.S. Pat. No. 6,772,760 and U.S. patent application Ser. No. 10/655,622, filed Sep. 5, 2003, each incorporated herein by reference in its entirety). These approaches supply an external source of energy, derived from the varying therapeutic gas pressure itself, to provide the energy required to counteract the distortion of the headgear, mask structures, and facial and nuchal tissues as the pressure rises.

Another way of reducing the discomfort and improving the seal of a respiratory mask is to use a quasi-toroidal air filled closed bladder as the sealing element. A traditional anesthetic face mask has a relatively thick walled and non-compliant quasi-toroidal air filled bladder. It requires great force to deform such a thick walled bladder to fit the patient's face. This is acceptable in an anaesthetized patient but not in a sleeping patient. A greatly improved closed quasi-toroidal bladder is very thin walled and compliant in the skin contact region, increasing gradually in thickness elsewhere, and supported by a rigid frame, as taught in PCT application No. PCT/AU2004/00563, filed Apr. 30, 2004, incorporated herein by reference in its entirety. A particular advantage of the thin-walled compliant skin contact region is that it provides medially directed pressure onto the nasal bones, whereas other prior art generally supplies only a posteriorly directed pressure, resulting in either leaks into the eyes or excessive force on the bridge of the nose or both. Such an improved bladder can be advantageously combined with any of the previously described methods which derive energy from the varying mask therapeutic pressure. A first disadvantage of such a thin-walled bladder is it has a tendency to slowly deflate during the night, due to leakage and/or diffusion of air through the very thin wall. A second disadvantage is that it does not, of itself, have a mechanism for deriving energy from the varying mask therapeutic pressure, and therefore cannot supply the energy required to counteract the distortion of headgear, mask structures, and facial and nuchal tissues as therapeutic pressure rises.

Accordingly, a need had developed to address the potential disadvantages of the prior art masks described above.

BRIEF SUMMARY OF THE INVENTION

One aspect is directed to a method, and corresponding apparatus, being applicable to a mask with a skin contact sealing element having a very thin-walled quasi-toroidal bladder, whose pressure can be adjusted to thereby adjust the sealing pressure applied to the underlying skin.

A further aspect of the invention is directed to a method/apparatus for causing a mask with a sealing element including a bladder, e.g., a hollow quasi-toroidal bladder, to seal comfortably against a patient's face across a range of therapeutic pressures.

One embodiment of the invention includes pressurizing a bladder to a pressure which exceeds an instantaneous therapeutic pressure by a positive offset amount, e.g., a positive constant offset amount, chosen so that the mask seals comfortably at any one therapeutic pressure.

The positive offset pressure may be provided in several forms. For example, the positive offset pressure may be provided by a weighted or spring-loaded piston; the recoil pressure of a balloon; a low impedance pump (e.g., a centrifugal or axial fan); a high impedance pump provided with a low impedance bypass (e.g., a spring-loaded blow-off valve and/or a water-trap blow-off valve); and/or at least one of a weighted or spring-loaded piston and/or a balloon, in parallel with a high impedance pump and/or an adjustable shunt (e.g., a valve, a spring-loaded blow-off valve, and/or a water-trap blow-off valve).

Another embodiment includes providing a sealing element with an inflatable bladder, and pressurizing the bladder to a pressure which exceeds an instantaneous therapeutic pressure by an amount that increases with increasing therapeutic pressure. The bladder pressure may be an affine function of mask therapeutic pressure.

These and other aspects/embodiments will be described in or apparent from the following detailed description of preferred embodiments.

BRIEF DESCRIPTION OF THE DRAWINGS

FIGS. 3A-3C are cross-sectional through various portions of the silicone cushion of FIG. 2, showing the thin-walled, quasi-toroidal bladder.

FIG. 3D is a cross-sectional view showing a port accessing the lumen of the bladder;

DETAILED DESCRIPTION OF EMBODIMENTS

Figure 1:
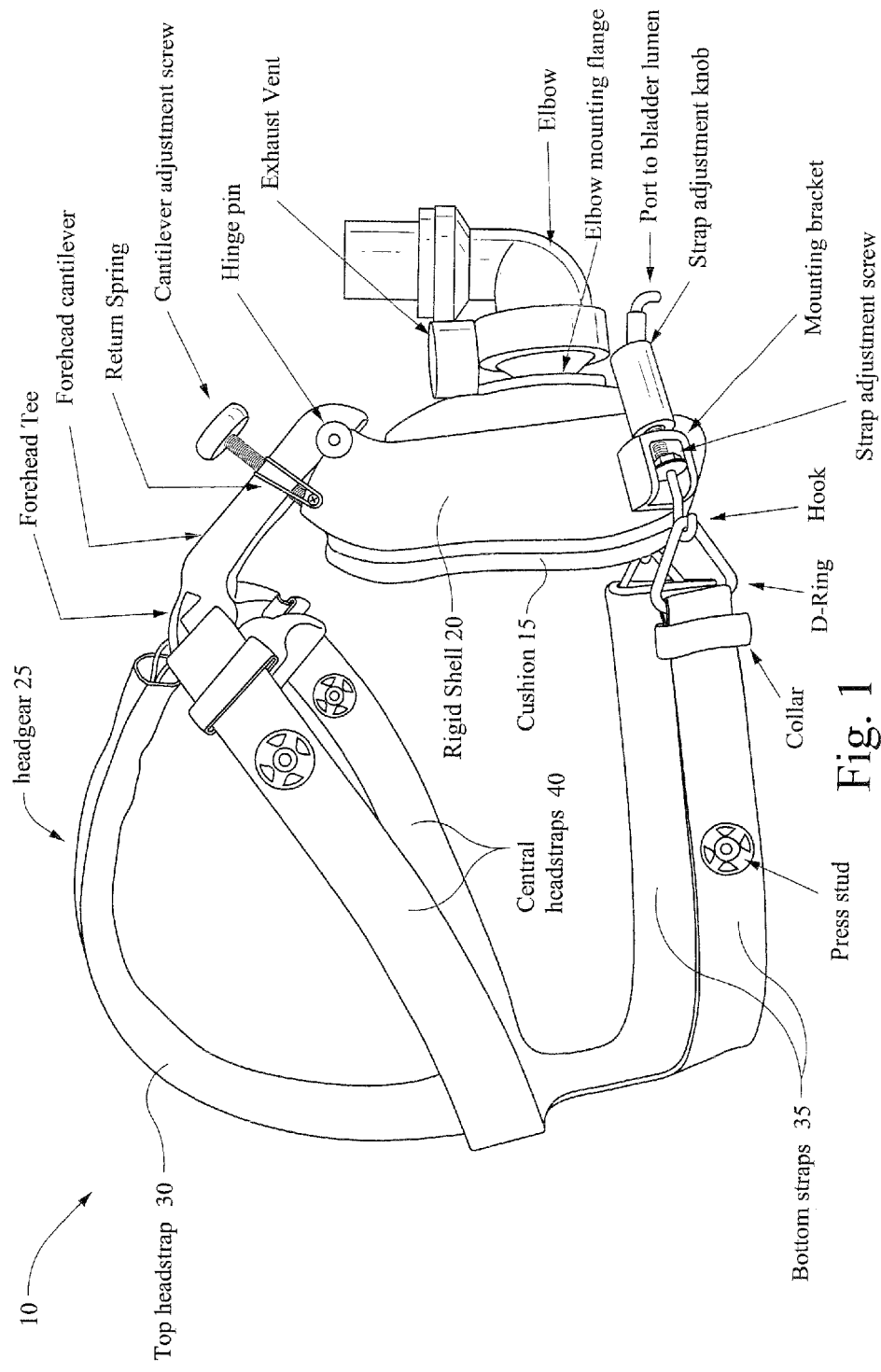
FIG. 1 shows a mask system according to an embodiment of the present invention.

FIG. 1 shows a mask system 10 according to an embodiment of the present invention. Mask system 10 includes a mask cushion 15, e.g., a translucent silicone mask cushion that is held in a frame, e.g., a rigid white polyurethane outer shell 20. Numerous other exemplary elements of the system are labeled in FIG. 1. The assembly of the mask cushion 15 and shell 20 is held against the patient's face using headgear 25 including one or more straps, e.g., a top headstrap 30, bottom headstraps 35, and/or central headstraps 40.

Figure 1A:
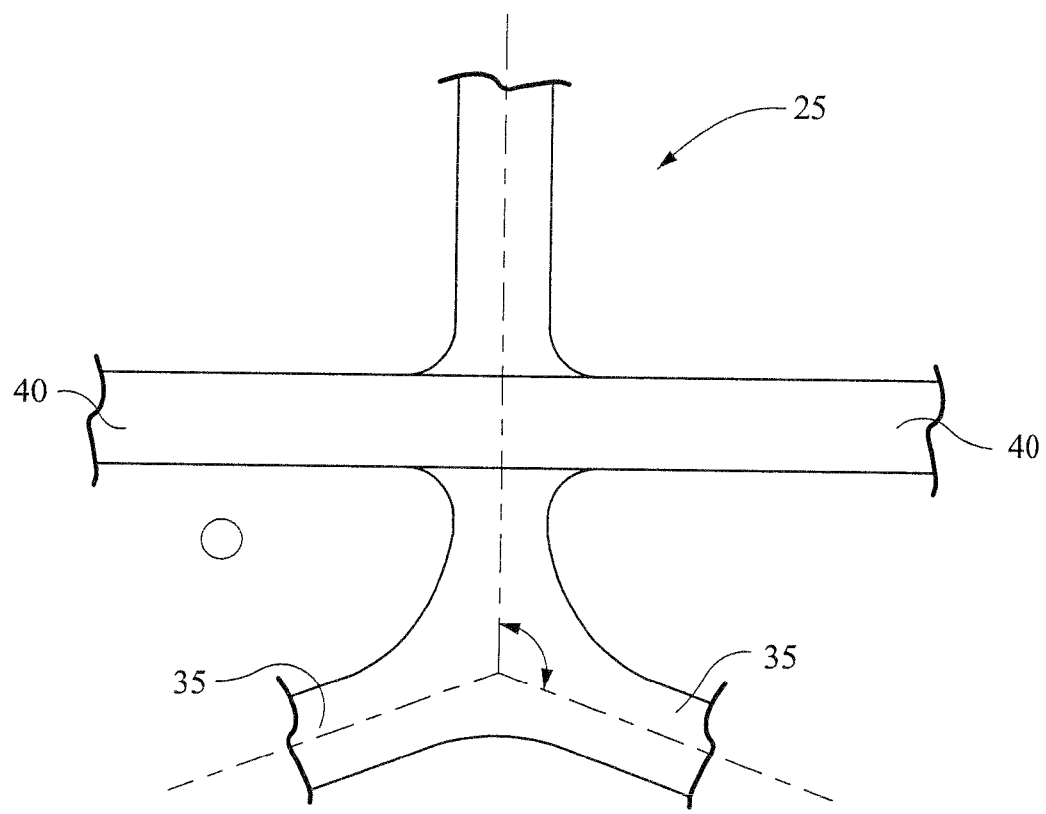
FIG. 1A is a partial rear view of the strap intersection at the rear of the patient's head.

FIG. 1A shows a partial rear view of the strap intersection. In this example, each bottom strap is at an angle of about 110° to the central (top) strap 30. The angle is chosen so as to allow for a much higher tension in the bottom straps 35 and much lower tension in the top strap 30. A greater angle will result in too much tension in the top strap, causing the mask to pull up painfully into the brow ridge, and leak into the eyes. A shallower angle will result in too little tension in the top strap, resulting in the mask digging painfully onto the sides of the nose.

All five straps preferably have two adjustment mechanisms. Firstly, they pass through a narrow polyurethane band, which provides a friction fit, enabling temporary adjustment. Secondly, they are held permanently in place with a press stud pushed through a hole punched with a hole-punch. Two prototypes were made, one with many pre-punched holes, and the other with a single hole punched in the correct place. The former is more suitable to home fitting by the end user; the latter is more suited to shop fitting by trained staff, because once set correctly, it cannot be fiddled with.

In addition, the bottom straps have screw adjustments, with a travel of ±1 cm, to allow very precise fine adjustment.

The bottom straps have a very simple quick release mechanism including a loop over a hook. This is intuitive, robust, and works fine.

To fit the straps, the patient should hold the mask in place with one hand, with no straps attached, and the mask pressurized. It should be noted that the current mask is worn much higher on the face than previous masks, and it should be checked that the top of the cushion is nuzzled in the groove between brow and nose. It is incorrect to place it with the top of the cushion on the nasal bridge itself, as is the case with existing masks.

Making sure that the forehead pads are pressing against the forehead, the adjustment screw on the cantilever for the forehead pad should then be adjusted until there is no leak at the extreme top of the bridge of the nose. This adjustment is only for the extreme top of the bridge of the nose, not for the cheekbones, or the sides of the nose. At this stage, the patient should be controlling all other leaks by selectively pressing on the mask ridge shell.

Once the mask is held in place and sealing, the central top strap should be set so that the "Y" (see FIG. 1A) point fits just under the occiput, as high as possible on the neck muscles. The bottom straps should then be tightened, until the patient can almost let go of the mask. The remaining two top straps are then tightened so that the forehead pads are being held pulled lightly but not excessively tightly against the brow.

After, the bottom straps should be further tightened until the patient can let go of the mask entirely. At this point, excess strap length should be cut off, leaving say 40 mm excess on each strap.

The positions of the ends of the straps can be marked with a marking pen. The headgear is removed. Making sure that the strap ends are at the marked points a belt rivet hole punch is used to put a hole near the end of each strap. A press stud may be inserted into the hole.

Final adjustment of the bottom strap screw adjustments may require the patient to adopt their normal sleeping position.

Figure 2:
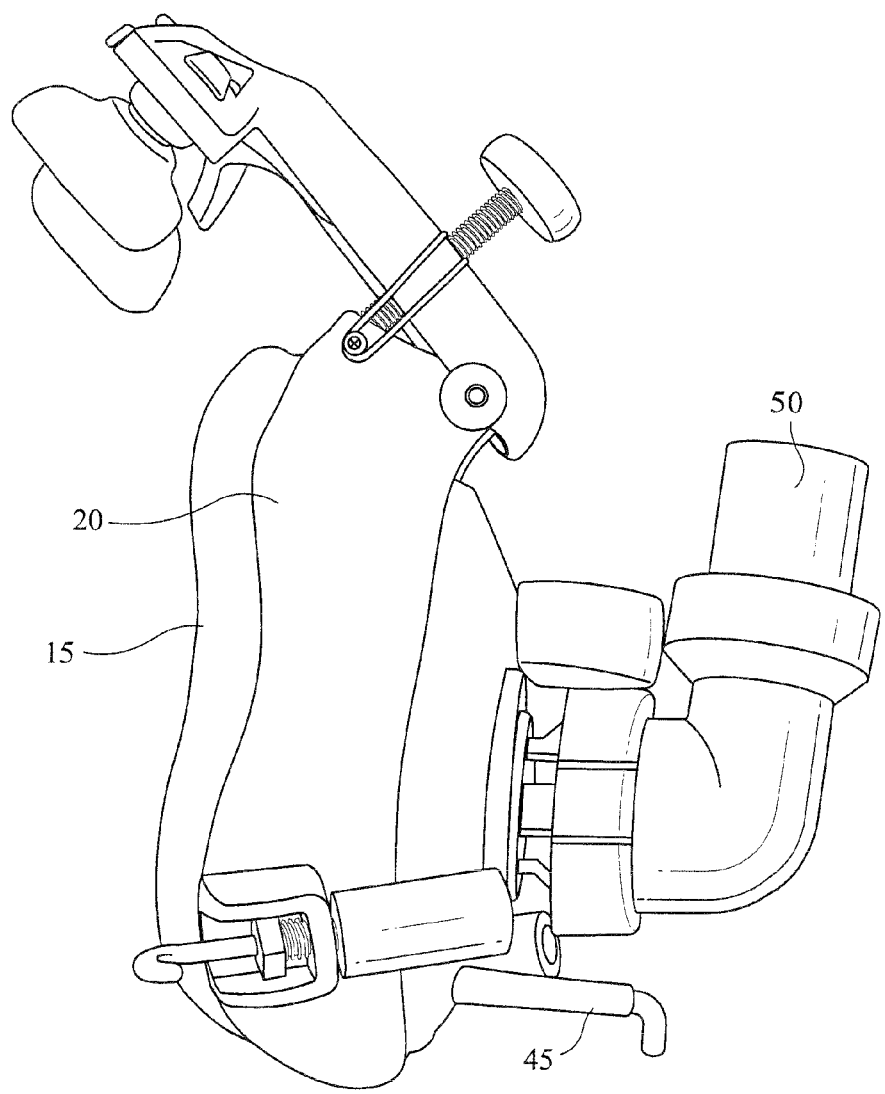
FIG. 2 shows an enlarged view of the cushion and shell of FIG. 1, without headgear.
Figure 3A:
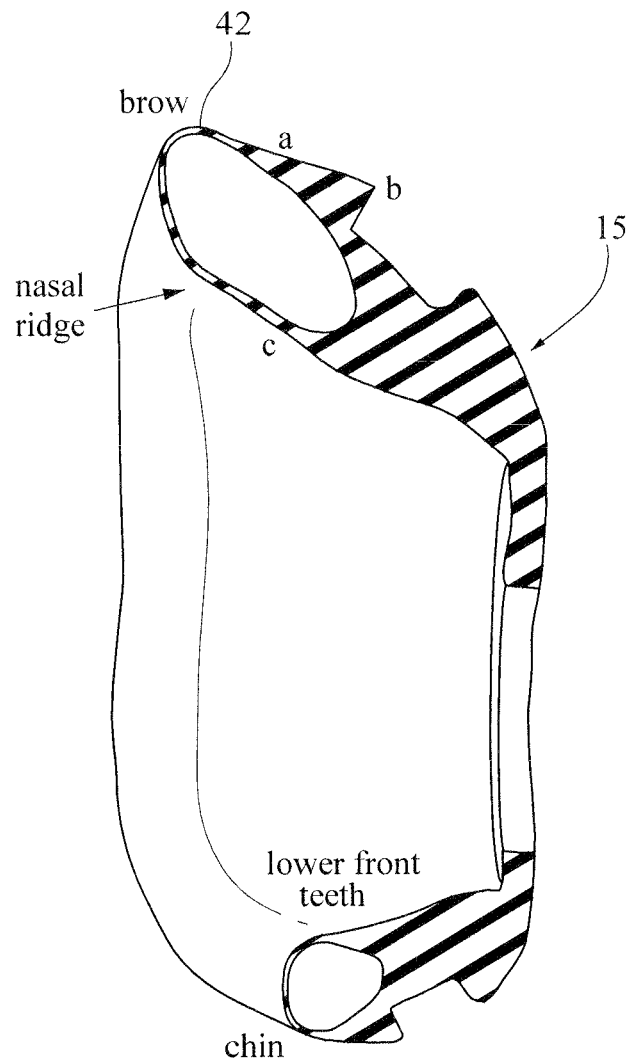

FIG. 2 shows an enlarged side view of the cushion and the shell of FIG. 1, without the headgear 25. Note port 45, which communicates with the lumen of the bladder. FIG. 3A shows a vertical cross-section through the mask cushion 15 of FIG. 2, showing a quasi-toroidal bladder, with walls which are very thin over the skin contact region, but progressively thicker elsewhere. The regions of the cushion 15 that contact the brow, nasal bridge, lower lip (over lower front teeth), and chin are marked. FIGS. 3B, 3C and 3D are cross sections of the bladder at the side of the nose, nostril and cheek region, respectively. Note again the port 45, communicating between the lumen of the bladder and the exterior, via which the pressure in the lumen may be externally controlled.

The cushion bears not so much on the bridge of the nose, but on the forehead immediately above the nose, with the top being nuzzled in the groove between the brow and nose. The wall thickness of the bladder increases progressively, so that it is relatively floppy where it contacts the skin, but much thicker where it joins with the shell, which is positioned only about 5 mm away from the skin surface, to contain any possible lateral movement of the bladder. In use, the patient's cheeks and chin press into the lower part of the bladder, thereby causing the bladder pressure to rise, which in turn causes the bladder to bulge inwards against the sides of the nose.

The region marked (a) in FIGS. 3A-3D shows a gradual thickening of the outer wall, so as to resist mask pressure causing outward herniation of the bladder. At the nasal bridge and chin, the gradual thickening starts much further out than elsewhere, so that the bridge and chin can bed into the cushion without excessive pressure.

The flange at (b) is to secure the cushion onto the rigid outer shell, e.g., as described in PCT application No. PCT/AU2004/00563, filed Apr. 30, 2004, incorporated herein by reference in its entirety. The region between (a) and (b) is preferably held stiffly in place and does not bend outwards under air pressure.

In FIG. 3B, a cross-section through the long side of the nose, the skin contact region (dotted line) presses medially inwards, not backwards. Again, this region should be as thin as is manufacturable, e.g., 0.35 mm or less. FIG. 3C is a cross-section through the nostril region of the patient.

The region marked (a) is in front of the eye, and does not touch the patient. It shows a gradual thickening, so that the side wall can resist the tendency of the bladder to herniate out laterally with high mask pressure.

Referring back to FIG. 2, note the port 45 (e.g. small silicone pipe) shown projecting from the antero-inferior surface of the cushion 15. Port 45 is in communication with bladder 42. A particularly suitable mask can be constructed using silicone with a durometer of 25 on the Shore A scale, and the skin contact portion of the wall of the bladder 42 should have a thickness of at most 0.5 mm.

For testing purposes, port 45 (FIG. 2) was connected to a T-connector (not shown), one arm of which was connected to a pressure transducer, and the other arm to a large syringe. The mask itself was pressurized to varying therapeutic pressures, increasing in steps of 5 $CmH_2O$ from 5 to 25 $CmH_2O$. Pressure was created by a conventional blower that delivers pressurized gas to elbow 50, typically via an air delivery tube.

At each therapeutic pressure, air was added or subtracted to pipe 45 using the syringe, until the mask just sealed. It was immediately apparent that, in order to just seal, the bladder pipe pressure was preferably about 5 $cmH_2O$ higher than the mask therapeutic pressure in each case. Thus, at a therapeutic pressure of 5 $cmH_2O$, the mask sealed with a bladder pressure of 10 $cmH_2O$, and at a therapeutic pressure of 25 $cmH_2O$, the mask sealed at a bladder pressure of 30 $cmH_2O$. If the bladder pressure was set to only 3 $cmH_2O$ above the therapeutic pressure, then the possibility of dynamic instability increased, which may cause the mask to buzz rapidly or creep slowly over the skin, with associated leakage of air and discomfort.

If the bladder pressure is set to 8 $cmH_2O$ above therapeutic pressure, then the seal can become somewhat more robust in the presence of gross body movement, but slightly less comfortable. At 10 $cmH_2O$ above the therapeutic pressure, the seal did not improve further, and was distinctly more uncomfortable.

During testing, it was further observed that if the subject wearing the mask, with inextensible polypropylene headgear of the configuration shown in FIG. 1, allowed the subject's mouth to open, so as to be in communication with, and at a similar pressure to, the air in the mask, and furthermore, to allow the muscles of the cheeks and lips to become flaccid, then the cheeks and lips bulge out away from the teeth and towards the mask cushion. This further improved the seal on the cheek and lower lip portions of the mask.

Furthermore, if the therapeutic pressure in the mask was 5 $cmH_2O$ and the bladder volume set to achieve a bladder pressure of 10 $cmH_2O$, and the therapeutic pressure was then increased to 25 $cmH_2O$, still allowing the mouth to fill with air and the cheeks to bulge out, then the bladder pressure would spontaneously increase to almost 30 $cmH_2O$, thus providing sufficient bladder pressure on the sides of the bridge of the nose to maintain a seal. Unfortunately, although subjects wearing the mask might be expected to perform this useful maneuver involuntarily during sleep, due to flaccidity of the musculature, most subjects appeared unable to perform a similar maneuver while awake, or if they could do so, would soon forget, and the seal would fail at all excepting the lowest pressures.

Note that in the experiments just described, the volume of air in the mask is being controlled, by squeezing the syringe. Conversely, according to preferred embodiments of the present invention, it is the pressure of air in the bladder that will be controlled. Thus, in embodiments of the present invention, although allowing the cheeks to billow out will help with the seal, it will not change the pressure in the bladder.

As mask therapeutic pressure rises, the headgear straps will tend to stretch somewhat, and also to dig into the subcutaneous tissues on the back of the neck. There will also be some compression of adipose tissue of the face, and some radial distortion of the bladder. These effects will all require that as therapeutic pressure increases, additional air enters the bladder in order to maintain a seal. Therefore, in order to overcome the finite compliance of the bladder wall, a graph of the minimum bladder pressure required to seal, plotted against therapeutic pressure, must in practice have a slope greater than unity. This must be particularly the case for an obese subject, or with relatively extensible headgear straps, or with an ill-fitting, incorrectly positioned, or less compliant bladder wall.

Figure 4:
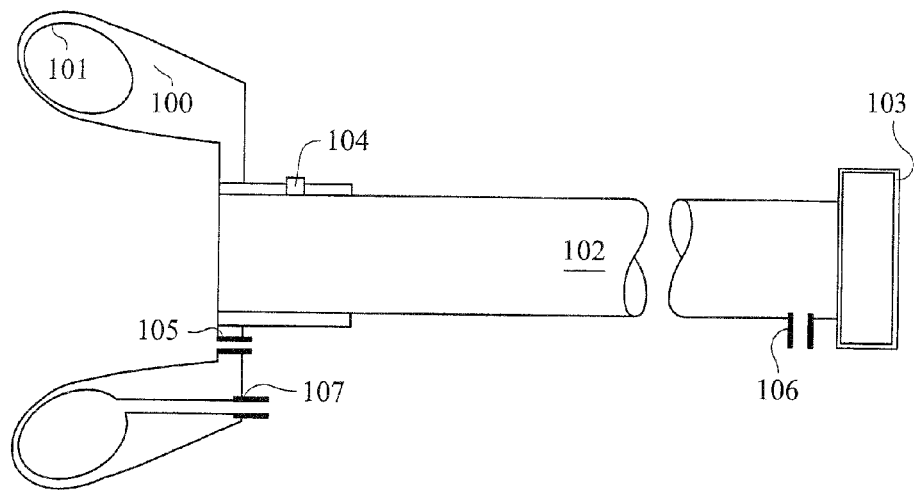
FIG. 4 shows a schematic view showing the assembly of a mask, an air delivery tube and a blower according to an embodiment of the present invention.

FIG. 4 shows a schematic cross section of a mask such as the mask in FIGS. 1-3D, showing external pneumatic connections. Cushion 100 contains a bladder, e.g., a quasi-toroidal thin-walled bladder 101. Main air inlet hose 102, typically a 2 meter length of standard 19 mm diameter ventilator hose, provides connection to a mechanical ventilator (blower) or similar source of breathable gas at controllable pressure (shown highly schematically as rectangle 103). Patient airflow exhaust is via exhaust vent 104. A port on the mask 105 permits measurement of the mask pressure. Alternatively, in the usual case where the impedance of main air inlet hose 102 is not great, an approximation of mask pressure may be conveniently taken from port 106 located closer to ventilator 103. There is a port 107, corresponding to port 45 in FIGS. 2 and 3D, which is in communication with bladder 101.

Figure 5:
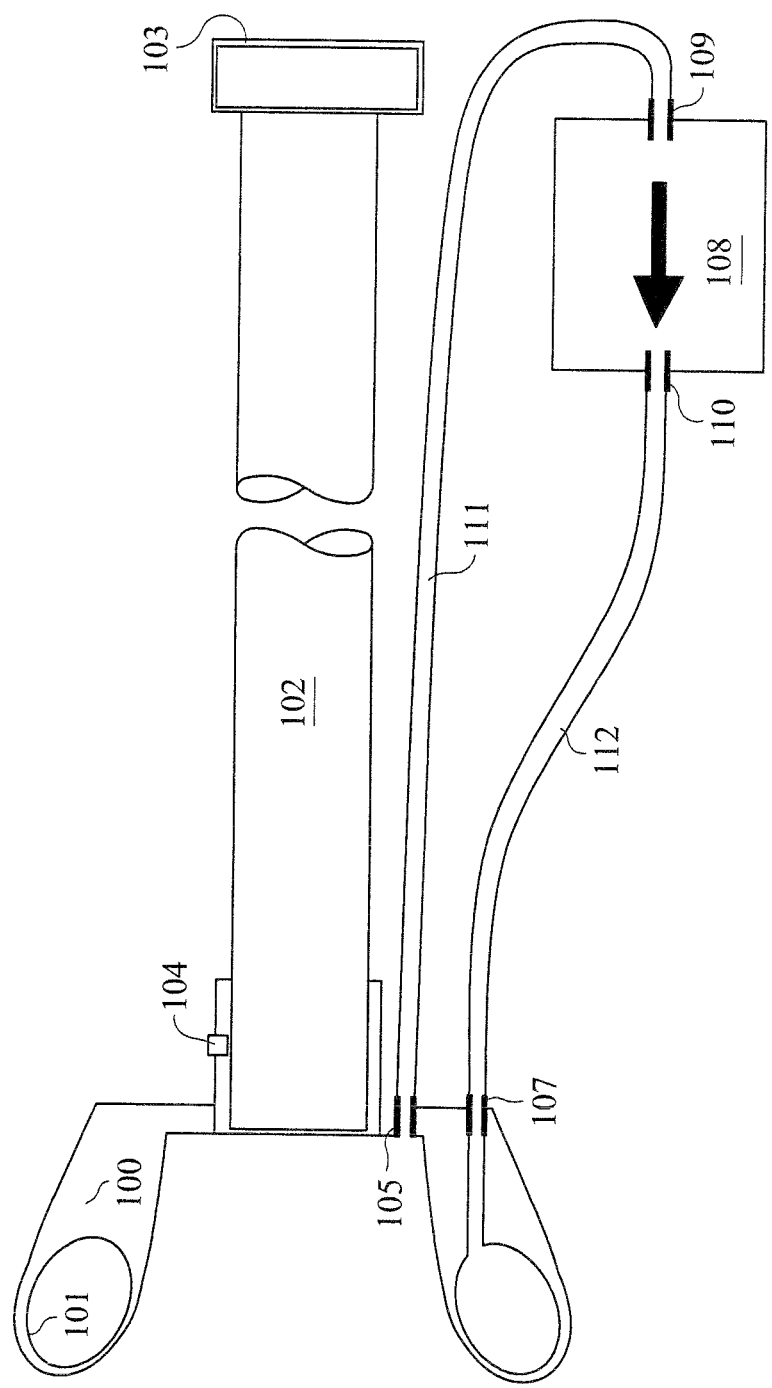
FIG. 5 is a schematic view of a source of positive offset pressure to be provided to cushion bladder, according to an embodiment of the present invention.

FIG. 5 shows an overview of an embodiment of the invention. A controllable source 108 of a fixed positive pressure difference maintains an adjustable fixed pressure gradient between a low pressure port 109 and a high pressure port 110. Low pressure port 109 is connected via hose 111 to port 105 on mask 100 such as shown in FIG. 4. High pressure port 110 is connected via hose 112 to port 107 on the mask. Port 105 is in communication with the therapeutic respiratory gas pressure in the body of the mask, and port 107 is in communication with quasi-toroidal thin walled bladder 101.

In its simplest conceptual form, source 108 is a low impedance pump, one example of which would be a high speed centrifugal or axial fan, generating a pressure gradient at zero flow which is adjustable in the range 0-10 $cmH_2O$, with a typical setting being 5 $cmH_2O$. The type of centrifugal fan, of diameter of the order of 8 cm, and operating at speeds of the order of 0-20,000 RPM commonly found in a bilevel ventilator or CPAP device is entirely suitable, but a much smaller motor can be used in the current application, because the required flow rate and therefore pneumatic work to be done is much less.

If source 108 is set to maintain port 110 at 5 cmH$_2$O above port 109 under conditions of near zero flow, then this will maintain the pressure of quasi-toroidal bladder 101 at approximately 5 cmH$_2$O above mask pressure, and for a typical mask of the type described above, this will maintain a comfortable seal across a wide range of mask pressures.

For example, consider the very typical case where the ventilator 103 is set to deliver a bilevel, or square wave, pressure profile, with an inspiratory pressure of Pi=25 cmH$_2$O, and an expiratory pressure of Pe=5 cmH$_2$O. Such settings would be suitable for a patient suffering from moderate to severe kyphoscoliosis during routine home therapy during sleep. During inspiration, the pressure in bladder 101 would be approximately 25+5=30 cmH$_2$O, and during expiration, the pressure in bladder 101 would be approximately 5+5=10 cmH$_2$O.

In general, if inspiratory pressure is Pi, expiratory pressure is Pe, and the excess pressure required to seal is 5 cmH$_2$O, the duration if inspiration is Ti, and the duration of expiration is Te, then the mean skin contact pressure will be $$P\text{skin}=((Pi+5)Ti+(Pe+5)Te)/(Ti+Te)$$

With a typical inspiration lasting 40% of the duration of the breath, this means that the mean pressure against the skin is 0.4×30+(1−0.4)×10=18 cmH$_2$O. Conversely, if the bladder were always inflated to a fixed pressure of 30 cmH$_2$O, sufficient to seal during inspiration, the mean pressure against the skin would be 30 cmH$_2$O throughout the cycle. Thus in this example, the invention affords a reduction in mean skin pressure of (30−18)/30=40%.

Notice that even with very stiff headgear straps, i.e., non-extendible headstraps, as mask and bladder pressure increase during inspiration, the mask strap tension will increase, and the strap will compress the tissues of the back of the neck. The bladder will increase in volume by of the order of 5-20 mL, depending on the degree of obesity of the subject, compensating for the compression of the tissues, and thus maintaining a seal. During expiration, the reverse will occur. The cycling of bladder pressure and volume does pneumatic work. If the change in bladder volume is dV, and the change in bladder pressure is (Pi+5)−(Pe+5)=Pi−Pe, then the work done is dV(Pi−Pe). Note that this is exactly the work done on the gas flowing through port 105, and therefore the energy is supplied by the ventilator, not by source 108.

Figure 6:
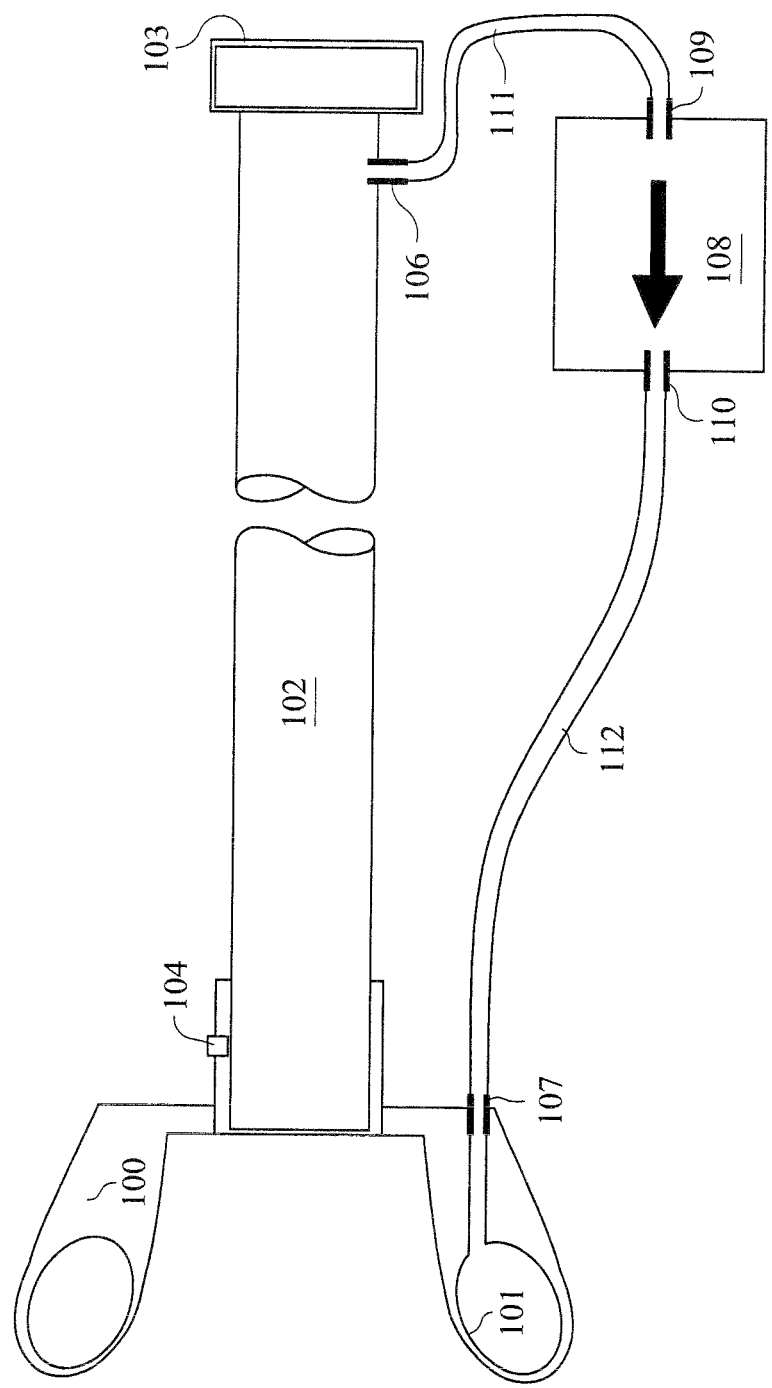
FIG. 6 shows an alternative pressure source arrangement according to an embodiment of the present invention.

FIG. 6 shows an alternative arrangement, in which hose 111 connects low pressure port 109 to port 106 which is in communication with the main air delivery hose 102, at any convenient point, for example close to the ventilator 103. This arrangement is particularly satisfactory for the typical case of a main air delivery hose 102 consisting of about 2 meters of standard 19 mm diameter respiratory air-hose, because the pressure at port 106 is slightly higher than at 107, by an amount which is higher in early inspiration than in early expiration. This helps overcome resistive losses in hoses 111 and 112 during flow dV.

Figure 7:
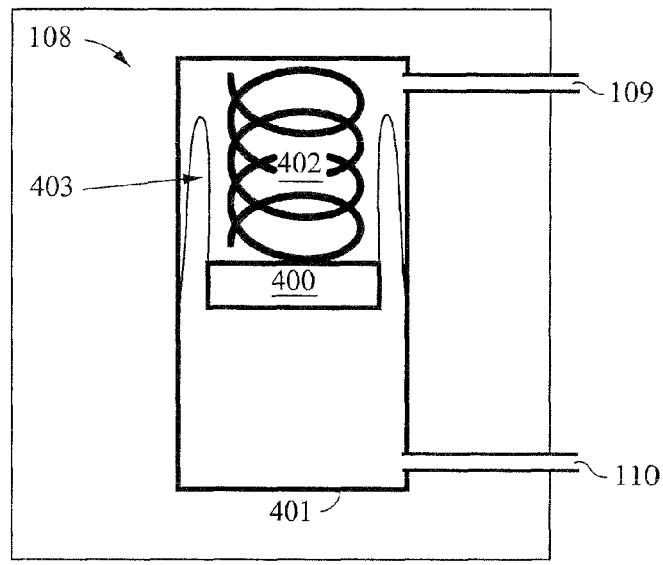
FIG. 7 shows a fixed positive pressure source according to an embodiment of the present invention.

FIG. 7 shows another passive embodiment of fixed positive pressure source 108, making use of the fact that the energy for the pneumatic work can be totally supplied by the ventilator. A piston 400 in a cylinder 401, pushed downwards by a compression spring 402, so as to generate a differential pressure between low pressure port 109 and high pressure port 110. For preference the piston has a rolling seal 403. For this embodiment, the wider the piston, and the longer the spring, the more steady will be the resultant differential pressure. A disadvantage of this very simple embodiment is that small leaks in the system, particularly in the bladder 101, will require the system to be reset from time to time. A typical silicone bladder with 0.5 mm wall thickness can leak its entire volume of about 70 mL in about 4 hours. A piston with a cross section of the order of 500 cm$^2$ and a travel of 1 cm will supply 500 ml, which is more than sufficient air for one night, providing there are no other leaks.

Figure 8:
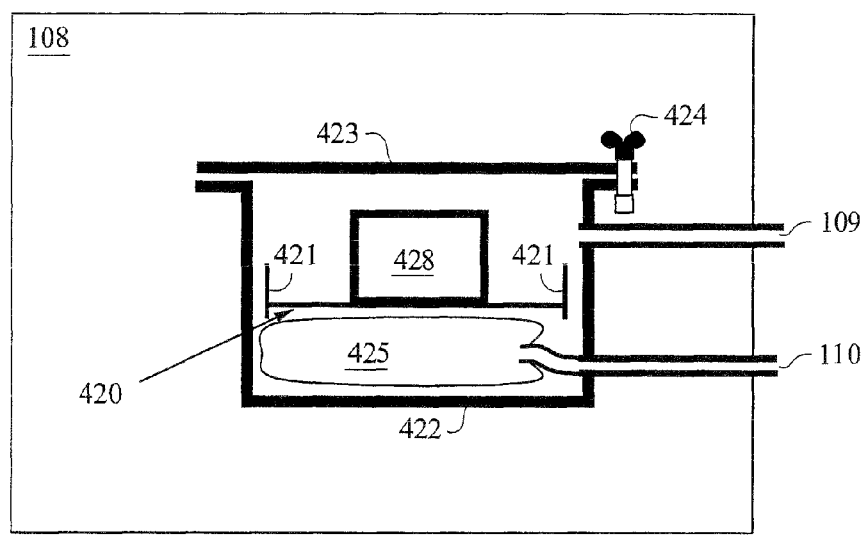
FIG. 8 shows a fixed pressure source according to yet another embodiment of the present invention.

FIG. 8 shows a variant of the embodiment of FIG. 7. Plate 420 slides freely on Teflon® guides 421 in box 422 with tightly sealing lid 423 held on with bolts 424. The plate presses on metallized thin-walled and therefore highly compliant Mylar® sac 425 connected via a tube through the wall of box 422 to high pressure port 110. Low pressure port 109 communicates with the region of box 422 external to the sac 425. A weight 428 presses downward on plate 420, thus providing a differential pressure between low pressure port 109 and high pressure port 110. The metallization of sac 425 reduces air loss through the wall of the sac. If the area of sac 425 in contact with plate 420 is 200 cm$^2$, and weight 428 is 1000 g, then a differential pressure of 5 cmH$_2$O will be produced between 109 and 110, as desired. To supply 500 ml total volume, the travel of the plate 420 will be 2.5 cm.

Figure 9:
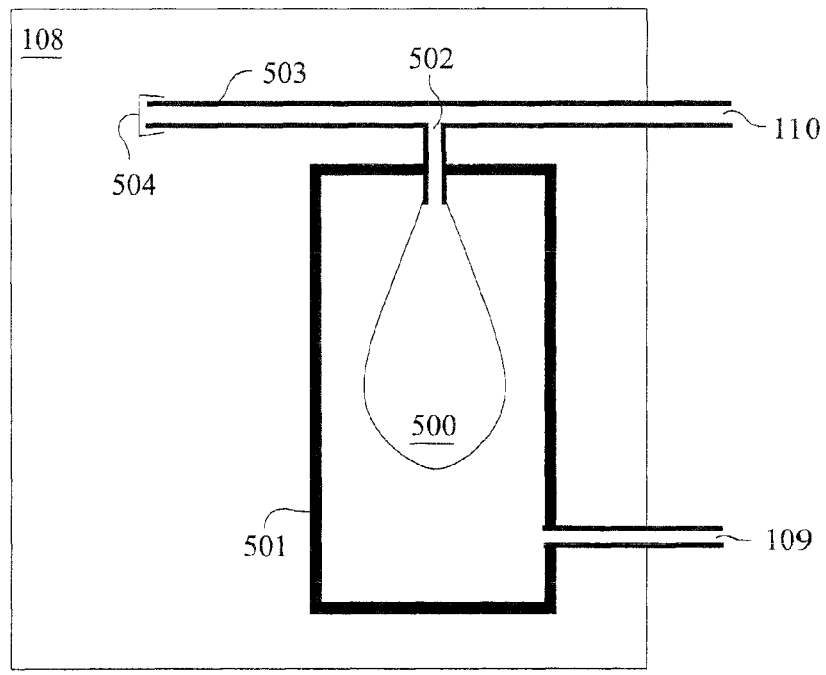
FIG. 9 shows a fixed pressure source according to another embodiment of the present invention.

FIG. 9 shows another embodiment of a fixed positive pressure source 108. An elastomeric balloon 500 is suspended in cylinder 501. The inside of the balloon communicates with high pressure port 110 via passage 502. The elastic recoil of the partially inflated balloon generates an adjustable pressure differential between low pressure port 109 and high pressure port 110. The balloon 500 may be refilled from time to time via port 503, which is otherwise closed by cap 504.

Figure 10:
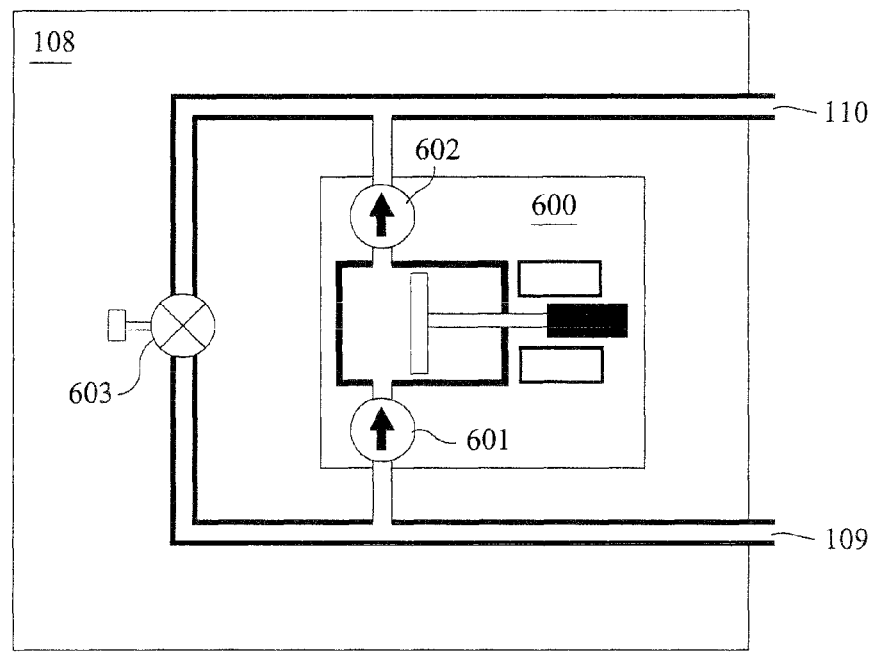
FIG. 10 shows a further embodiment of a fixed positive pressure source.

FIG. 10 shows still another embodiment of a fixed positive pressure source 108, in which a main frequency solenoid actuated diaphragm type high impedance pump, shown schematically as box 600, with inlet port 601 and outlet port 602, is fitted with adjustable shunt valve 603. The flow of air generated by pump 600 through shunt valve 603 causes a differential pressure to appear between low pressure port 109 and high pressure port 110. In use, the mask is donned, the ventilator started, and the shunt valve is opened or closed until sufficient differential pressure is achieved to cause the mask to seal. For more precise control of the differential pressure, shunt valve 603 can be replaced with a spring-loaded blow-off valve. A water-trap blow-off valve (in which the inlet pipe is placed, for example, 5 cm below the surface of a sealed jar of water, and the outlet pipe is taken from the region above the water) can also be used.

Figure 11:
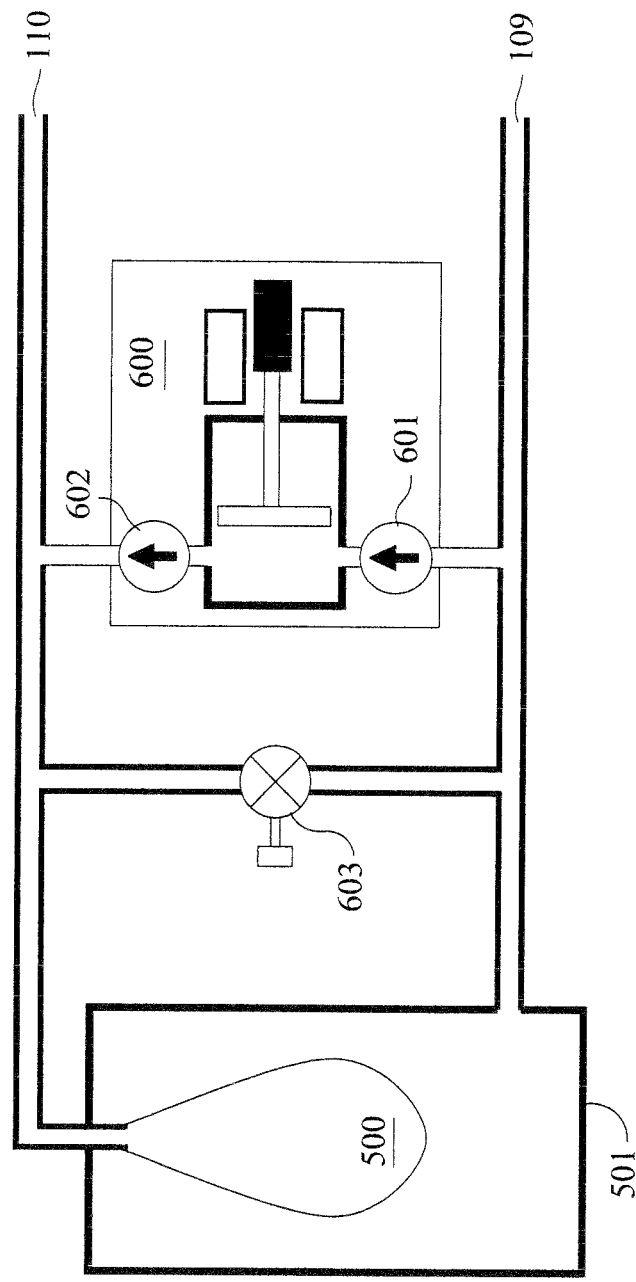
FIG. 11 shows an adjustable differential pressure source according to a further embodiment of the present invention.

FIG. 11 shows yet another embodiment of an adjustable differential pressure source 108, in which a balloon 500 in cylinder 501 is placed in parallel with diaphragm pump 600 and adjustable shunt resistance valve 603. The flow of air from diaphragm pump 600 through adjustable shunt resistance valve 603 causes an adjustable differential pressure between low pressure port 109 and high pressure port 110. Elastomeric balloon 500 in cylinder 501 provides a low impedance path between 109 and 110 at high frequencies, thus removing high frequency oscillations induced by the action of the pump, and further helping keep the differential pressure constant at the respiratory rate.

Of the embodiments described, the most satisfactory include the low impedance centrifugal fan or the balloon, shunt, and high impedance pump, the choice between the two being dependent on cost and convenience only.

As described above, it will be optimal to cause the bladder pressure to rise slightly faster than mask therapeutic pressure. For example, for a particular patient and mask combination, the mask may seal at a therapeutic pressure of 5 cmH$_2$O when the bladder pressure is 8 cmH$_2$O, a difference of 3 cmH$_2$O, but a therapeutic pressure of 25 cmH$_2$O might require a bladder pressure of 33 cmH$_2$O, a difference of 8 cmH$_2$O. In general, the positive offset pressure of the bladder can be in the range of 1-10 cmH$_2$O, or more, depending on application. Thus, an improvement over a fixed pressure difference between bladder pressure P$_{bladder}$ and mask therapeutic pressure P$_{therapeutic}$ would be:

$$P_{bladder} = K_0 + K_1 P_{therapeutic}$$

where, for the particular example given, slope K$_1$=1.25, and intercept K$_0$=1.75 cmH$_2$O.

In full generality, bladder pressure can be set to any desired function of mask pressure, using any controllable pressure source, a pressure transducer, and a suitable controller.

The pressure transducer measures instantaneous mask pressure and produces a mask pressure signal. In some cases, this signal may be directly available already from the main ventilator that supplies breathable therapeutic gas to the mask. The mask pressure signal is then fed to a controller, for example a microcontroller, linearizing amplifier, operational amplifier with adjustable gain and offset, or the like, the output of which is the desired bladder pressure signal. The bladder pressure signal is then fed to the controllable pressure source. For example, the controllable pressure source can be a motor-driven fan with a suitable open loop controller to accept bladder pressure signal as input and generate the motor speed required to produce the desired pressure, or it can be a closed loop controller, comparing the desired pressure signal with the actual bladder pressure measured using a second pressure transducer.

A servo-controlled fan, using a differential pressure transducer, can be configured to produce a bladder pressure equal to mask pressure plus a fixed offset as follows. Bladder pressure is connected to the (+) input of the differential pressure transducer. Mask pressure is connected to the (−) input of the differential pressure transducer. The pressure transducer now produces a signal equal to the difference between bladder and mask pressures. This signal is now fed to the (−) input of a servo-amplifier, and the desired pressure offset signal (e.g. 5 cmH$_2$O) is fed to the (+) input. The servo-amplifier output is fed to the fan motor.

Figure 12:
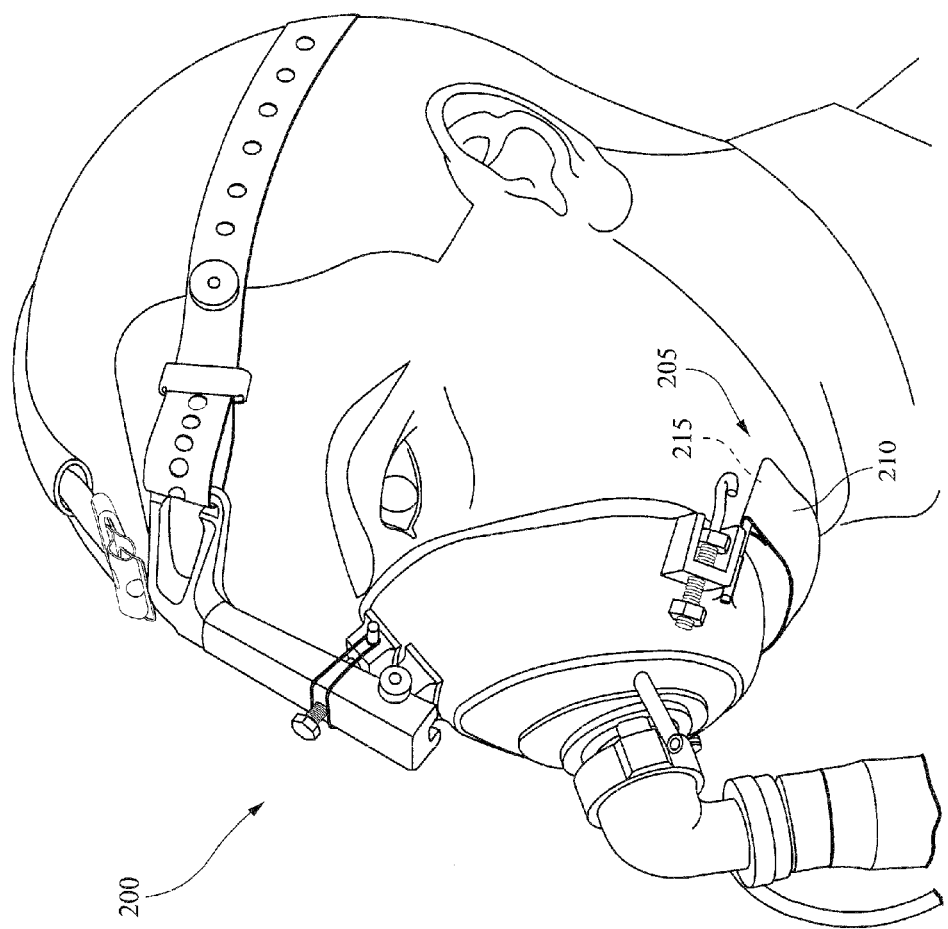
FIGS. 12-14 illustrate a chin strap assembly according to an embodiment of the present invention.

FIG. 12 is a perspective view of a mask assembly 200 that is similar to the mask assembly shown in FIG. 1, in use on a patient. One of the main differences is that mask assembly 200 includes a chin strap assembly 205 that includes a chin strap 210 and one or more supports 215.

Figure 13:
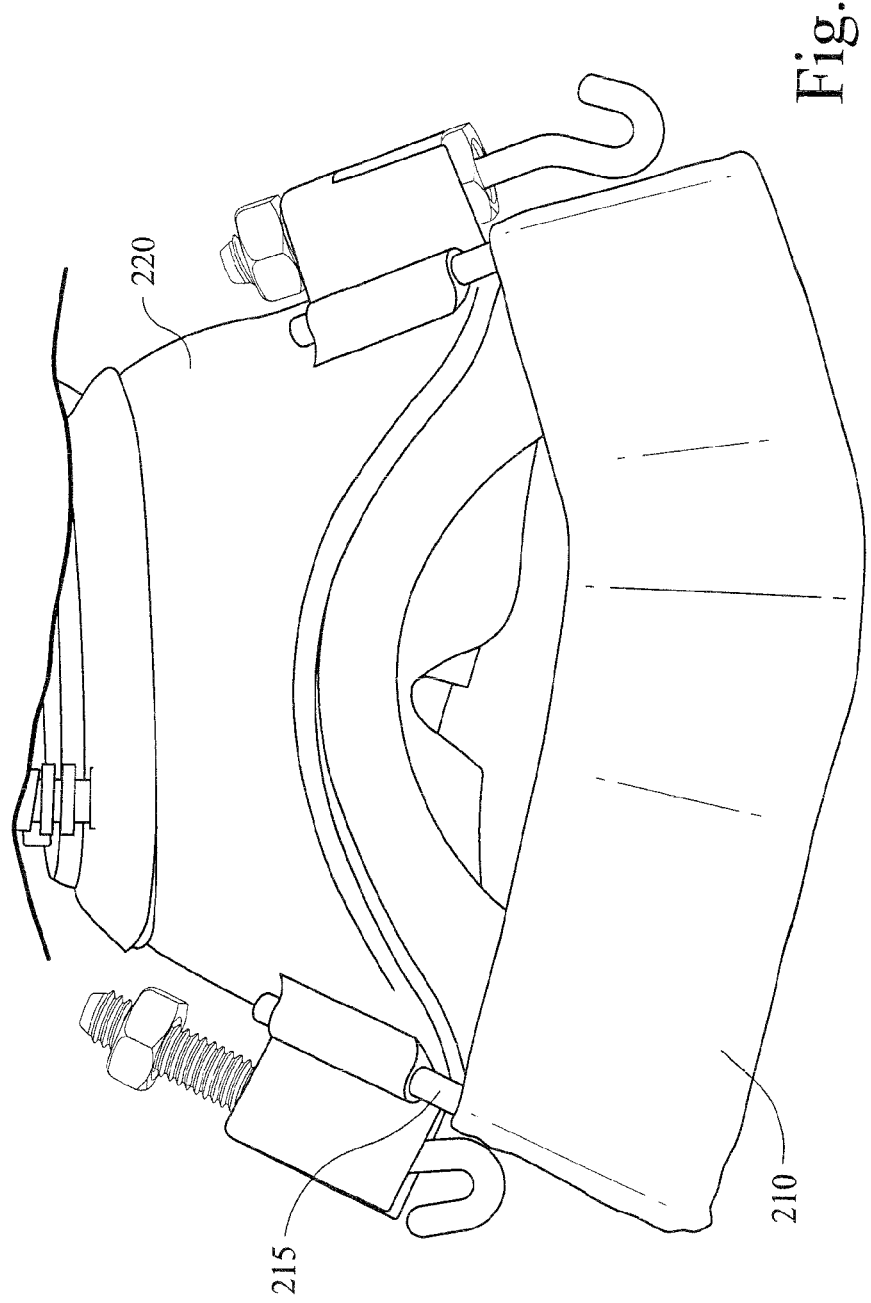
Figure 14:
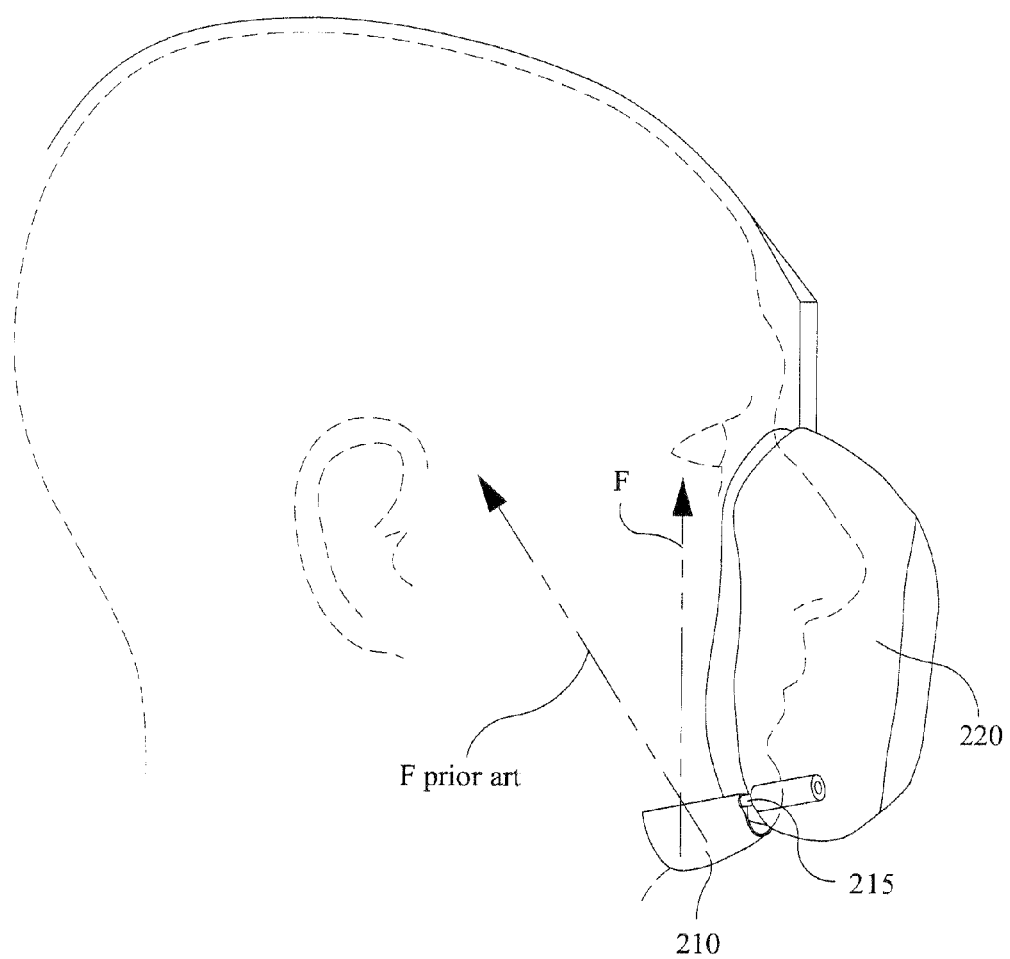

FIG. 13 shows a bottom view of a portion of the mask assembly 200, highlighting the chin strap assembly 205. In FIG. 13, the strap 210 has been pulled slightly away from the shell 220, thereby revealing the support 215. Support may be fixedly or selectively attached to shell 220. The chin strap serves three quite distinct purposes. Firstly, it helps prevent the mouth from passively coming open and falling out of the mask, for example in rapid eye movement sleep. Secondly, when the mouth fills with air at or near mask pressure, the floor of the mouth acts as a piston, generating a downward force on the jaw. At high mask pressure, this downward force can considerable. The chinstrap helps prevent downward movement of the jaw due to the pressure of the air in the mouth. Thirdly, the reaction force in the chinstrap pulls downward on the mask. This in turn helps push the mask downward onto the nasal bones, thus helping with the seal. The user can adjust this effect by tightening or loosening the top strap of the headgear 25, which attaches to the top of the mask. The effect of the overall geometry of top strap, rigid shell of mask, and chin strap is to produce a generally vertical force F on the chin, thus preventing the jaw from descending without applying a backward component, whereas a conventional chinstrap, passing over the top of the ear, produces a large backward component to the force on the jaw (F$_{(prior\ art)}$), which is both mechanically inefficient at stabilizing the jaw, injurious to the temporomandibular joint, and can occlude the pharyngeal airway. Some prior art masks include a fixed, built-in support for the jaw, which will produce the same benefits as the chinstrap described here. However, in embodiments of the present invention, the chinstrap is for preference adjustable, for example by using Velcro or similar hook-and-loop tape, so as to allow comfortable adjustment of the position of the jaw.

The invention has been described in the context of high level non-invasive ventilatory support for respiratory failure, central sleep apnea, etc. However, it may be used wherever a very precisely sealing mask is required, for example in dusty or polluted industrial environments, workshops, and aerospace applications.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The invention claimed is:

1. A patient interface comprising:
   a frame;
   a cushion provided to the frame and defining a chamber structured to be in communication with a first source that is adapted to provide a first pressure to the chamber; and
   a bladder associated with the cushion and configured to engage a face of a patient, the bladder having a side wall, and the side wall being thinner in a face contacting region of the bladder than in a face non-contacting region, the side wall thickness being progressively thicker from the face contacting region to the face non-contacting region,
   wherein a rate of change in the thickness of the side wall varies around the face contacting region of the bladder, and
   wherein the bladder is configured to be in communication with a second source that provides a second pressure to the bladder that is higher than the first pressure by a positive offset amount.

2. The patient interface of claim 1, wherein the bladder is configured to receive gas from the chamber.

3. The patient interface of claim 2, wherein the chamber is configured to be in fluid communication with both the first and second sources.

4. The patient interface of claim 3, wherein the chamber comprises an inlet port configured to be in fluid communication with the first source and comprises an outlet port configured to be in fluid communication with the second source.

5. The patient interface of claim 4, wherein the bladder includes an inlet port configured to be in fluid communication with the second source.

6. The patient interface of claim 1, wherein the positive offset amount is fixed.

7. The patient interface of claim 6, wherein the positive offset amount is about 5 cmH$_2$O.

8. The patient interface of claim 1, wherein the bladder is configured such that the second pressure variably changes with changes in the first pressure.

9. A mask assembly according to claim 8, wherein the offset amount ranges from about 1-10 cmH$_2$O.

10. A mask assembly according to claim 9, wherein the offset amount ranges from about 3-8 cmH$_2$O.

11. A mask assembly according to claim 1, wherein the offset amount is dependent on a therapeutic pressure.

12. A method for sealing a patient interface with respect to a patient, comprising:
    engaging the patient's face with the interface of claim 1 so that the bladder engages the patient's face in the face contacting region;
    providing a first pressure to the chamber of the interface; and
    pressurizing the bladder to a second pressure that exceeds the first pressure applied to the chamber of the patient interface such that the patient interface seals comfortably at any instantaneous pressure applied to the chamber of the patient interface.

13. The method of claim 12, wherein a difference between the first pressure and the second pressure is kept constant.

14. The method of claim 13, wherein the difference between the first pressure and the second pressure is achieved by at least one of a spring-loaded piston, a recoil pressure of a balloon and an impedance pump.

15. An apparatus comprising:
    a first source configured to deliver a breathable gas at a first pressure to a patient;
    a patient interface comprising:
        a frame;
        a cushion provided to the frame and defining a chamber, the cushion being adapted to engage a patient's face and being structured to be in communication with the first source; and
        a bladder contained within the cushion, the bladder having a side wall that is thinner in a face contacting region of the cushion than in a face non-contacting region of the cushion, the side wall thickness being progressively thicker from the face contacting region to the face non-contacting region; and
    a second source configured to deliver gas at a second pressure to the bladder that is higher than the first pressure by a positive offset amount,
    wherein a rate of change in thickness of the side wall of the bladder varies around the face contacting region of the cushion.

16. The apparatus of claim 15, wherein the first source is a blower.

17. The apparatus of claim 16, wherein the second source comprises a spring-loaded piston.

18. The apparatus of claim 16, wherein the second source comprises a balloon and the positive offset amount is generated by a recoil pressure of the balloon.

19. The apparatus of claim 16, wherein the second source comprises an impedance pump.

20. The apparatus of claim 19, wherein the impedance pump includes at least one of a centrifugal fan and an axial fan.

21. The apparatus of claim 16, wherein the second source comprises an impedance pump provided with an impedance bypass that is configured to remove oscillations induced by the impedance pump.

22. The apparatus of claim 21, wherein the impedance bypass comprises an adjustable shunt valve and/or at least one of a spring-loaded piston and a balloon, in parallel with the impedance pump.

23. The apparatus of claim 21, wherein the impedance bypass comprises at least one of a spring-loaded blow-off valve and a water-trap blow-off valve, and/or at least one of a spring-loaded piston and a balloon, in parallel with the impedance pump.

24. The apparatus of claim 16, wherein the second source is configured to generate a constant positive offset pressure over an entire range of first pressures.

25. The apparatus of claim 16, wherein the second source is fluidly connected to an outlet of the first source at a position upstream of the chamber of the patient interface.

26. The apparatus of claim 16, wherein the second source is fluidly connected to an outlet of the patient interface.

* * * * *